United States Patent [19]

Danisch

[11] Patent Number: 5,321,257

[45] Date of Patent: Jun. 14, 1994

[54] FIBER OPTIC BENDING AND POSITIONING SENSOR INCLUDING A LIGHT EMISSION SURFACE FORMED ON A PORTION OF A LIGHT GUIDE

[76] Inventor: Lee A. Danisch, Comp. B-4 Site 9 R.R. #6, Fredericton, New Brunswick, Canada, E3B 4X7

[21] Appl. No.: 915,283

[22] Filed: Jul. 20, 1992

Related U.S. Application Data

[63] Continuation-in-part of Ser. No. 738,560, Jul. 31, 1991.

[51] Int. Cl.⁵ .............................. G02B 6/10
[52] U.S. Cl. ................... 250/227.16; 385/13
[58] Field of Search ............ 250/227.16, 227.14; 385/12, 13

[56] References Cited

U.S. PATENT DOCUMENTS

| | | | |
|---|---|---|---|
| 3,801,389 | 4/1974 | Fujimura | 156/6 |
| 4,880,971 | 11/1989 | Danisch | 250/227 |
| 5,005,005 | 4/1991 | Brossia et al. | 340/604 |

*Primary Examiner*—Jack I. Berman
*Assistant Examiner*—James Beyer

[57] ABSTRACT

A bending, and position, sensor is composed of a fiber optic or light wave guide, for attachment to the member which is to be bent, or displaced. Light is injected at one end and detected at the other end. Bending of the fiber results in light loss through a surface strip or band, along one side of the fiber, this loss being detected. The loss of light detection is used to produce indication of bending or displacement. Two or more light guides can be oriented to give indication of direction of bending, or displacement.

25 Claims, 10 Drawing Sheets

SECTION X-X

SECTION Y-Y

SECTION Z-Z

FIBER OPTIC BENDING AND POSITIONING SENSOR INCLUDING A LIGHT EMISSION SURFACE FORMED ON A PORTION OF A LIGHT GUIDE

This is a continuation-in-part of application Ser. No. 07/738,560, filed Jul. 31, 1991.

This invention relates to fiber optic bending, and positioning, sensors, and in particular is concerned with the use of a fiber optic light guide of a particular form, to guide, and indicate, bending and displacement.

BACKGROUND OF THE INVENTION

1. Field of the Invention

Various methods exist for measuring bending of structural members. One well-known method is to measure stress on or in the members using resistive strain gauges arranged on the surface in patterns such that the bending can be inferred from a knowledge of the modulus of elasticity of the member. Under some conditions it is advantageous to measure stress or deformation using optical fibers. Advantages over electrical methods include immunity from electrical interference, light weight, ability to resist chemical attack, and operation at high temperatures. Applications include measuring and controlling vibration, sag, and deflection in aircraft wings, helicopter rotors, sailing vessel masts, large structures, machinery, boiler tubes, and robotic arms. Other applications include measuring the position of control pedals, active wing surfaces, rudders, and the like.

It is possible to embed optical fibers in composite structures so that they perform a combination of structural and sensing functions. For this purpose it is advantageous to have sensors that are unbent when at rest, so that they can lie parallel to many other straight fibers.

2. Description of the Related Art

Many types of optical fiber sensors have been developed for the measurement of stress and position. Most employ interference techniques to measure changes in length or bend radius of the fiber. Most of these techniques rely on detecting standing waves set up in the fiber by reflecting part of the light back from its distal end. These techniques are very sensitive (comparable to strain gauges) but require complex and expensive measurement techniques such as interferometry or optical time domain reflectometry (OTDR) for their execution. Measurements are very sensitive to changes in temperature, requiring elaborate compensation techniques. Another limitation of many of the interference techniques is insensitivity to direction because the measurement is made by counting the number of interference peaks due to distortion of a fiber. Thus, for example, shortening of the fiber is indistinguishable from elongation, or bending up is the same as bending down; unless the fibers are arranged in appropriate curves or other special geometric arrangements.

Equipment for performing interference measurements tends to be bulky and expensive, requiring frequent adjustment. It must be capable of distinguishing peaks at spacings of the order of 0.5 to 1 micron or less. This has limited most fiber optic stress measurements to tests which can be performed under carefully controlled laboratory conditions.

Non-interference techniques can be used to measure bending in fiber optics. It is well known that light leaks out of the core of an optical fiber if it impinges on the cladding at a sufficiently large angle with respect to the long axis of the fiber. For every fiber, there is a critical angle dependent on the indices of refraction of core and cladding, beyond which light will escape. If the fiber is bent, some of the light in the core will exceed this angle and escape. This effect has been used to build "microbending" sensors, which simply measure the percentage of transmission of light down a fiber. These suffer from relative insensitivity (little light is lost) at small angles. Usually a microbend sensor consists of a fiber placed in a corrugated fixture such that a force applied to the fixture will create many sharp bends in the fiber. Microbend sensors are used to measure pressures, forces, and displacement. These sensors also do not measure the direction of the force unless pre-tension is applied.

Other fiber optic sensors have been constructed in which the cladding is removed from the core, or the cladding and some of the core are etched away. These sensors may be more sensitive to bending than untreated fibers, but, like other bending sensors mentioned above, give no information about the direction of a bend unless they are bent at rest. They are thus unsuitable for incorporating in a simple manner in composite structures containing many parallel fibers with sensory and structural properties.

Other fiber optic sensors have been constructed which use thin films in place of the cladding, to give location information based on the wavelength of the filter produced by the thin film. This technique shows no improvement in sensitivity over other fiber optic sensing techniques, so interference techniques must be used to obtain useful outputs.

SUMMARY OF THE INVENTION

The present invention uses fibers having a light emission surface extending in a thin band along one side of the fiber only. This surface can merely be the exposed surface of the fiber core or the exposed surface can be textured, for example, have serrations, corrugations or other roughness. This leads to bending or position sensors with particular characteristics. In all cases, including where the surface of the fiber is merely exposed and when the surface is textured, the light transmitted increases for bends in which the light emission surface becomes concave outward from the axis of the fiber, and decreases when it becomes concave inward. The percentage change of light for bends in the plane of maximum sensitivity is greater for textured surface fibers than for untreated fibers, but both provide measurement with simple instrumentation for small angles of bend. The sensitivity is approximately that obtainable with resistance strain gauges, but the sensor requires no elongation of the material to which it is mounted to obtain a response. The sensor could be located along the neutral axis of a bending beam, and still indicate bending angle.

Conventionally, fibers are composed of a core and a cladding, usually with a buffer layer and a jacket placed over the cladding to protect it. The exposed surface referred to is the exposed core. The fiber can be fused quartz, or of plastic material.

A sensor made in this way has distinct advantages over other fiber optical sensors used to measure displacement or bending. A single, straight fiber treated in this way can be used to measure very small angles of bend, using simple instrumentation which measures only the percentage of light passing from one end of the fiber to the other. The same single fiber sensor indicates direction of bending, so that two or more parallel fibers attached to a structure and arranged to have maximum sensitivity planes at angles to each other could be used to measure the bending vector, indicating magnitude and direction in three-space of the bend. A triplet of fibers arranged to have axes of maximum sensitivity at 120° to each other is analogous to a strain gauge rosette, which measures the strain vector in the plane of the rosette gauge.

Fibers having roughened or similar surfaces for light emission are described in U.S. Pat. No. 4,880,971 in the name of the present applicant.

Broadly, in accordance with the present invention a fiber optic bending, and positioning, sensor comprises a fiber optic light guide having a light emission surface extending in a relatively thin band on one side of the fiber for at least part of its length. Such surface can be the bare surface of the fiber core with the cladding coating, and buffer layer if present removed locally, or the surface can be textured by serrations, etching, or abrasion or other, such that light can leak out through only that portion of the circumference of the fiber. Lengths of fiber beyond the part having the emission surface serve as light guides to convey light to and from the part. The emission surface is positioned so that bending of the fiber affects the light transmission effect of the surface.

The amount of light is measured by standard techniques. One such technique would employ a light emitting diode at one end of the fiber, and a photodiode at the other. It is not necessary to use special mode-enhanced fibers or special light sources. The light may be monochromatic or of broad spectrum. It is possible to embed the fiber in a composite material such as a carbon-fiber/epoxy matrix. This has been successfully demonstrated with treated plastic, glass or silica core fibers embedded in epoxy adhesive, with little change in sensitivity of response to bending compared to a non-embedded fiber. In some situations it may be desirable to coat or otherwise cover the emission surface to prevent leakage of light to other sensors or to compensate for optical characteristics of the matrix material. Examples of coatings would include semi-opaque adhesives with a high index of refraction, graphite or dye-filled epoxies, a surrounding metal or plastic sleeve filled with epoxy, and heat-shrinkable tubing. It is possible to employ fibers of virtually any diameters. Fibers with core diameters of 0.125 to 1.0 mm have been used.

Bending changes the portion of light able to escape from the emission surface, in such a way that bends which make the treated region concave outward decrease the loss of light, and opposite bends increase the loss of light. The strip of emission surface of the fiber can vary in length from a few millimeters to meters. The output signal will represent the average bend of the strip. The application of torsion and axial tension to the fiber have negligible effect on the output. The only important input is bending. The fiber is very limp in bending, and responds only to bending angle, not to elongation of the member to which it is attached. Therefore it requires virtually no force to produce an output.

An amplifier would be used to detect the amount of light falling on the photodetector. Standard techniques can be used to improve sensitivity. One method that has been used is to chop the light by rapidly turning on and off the light emitting diode, and employing synchronous detection in the amplifier. This has the advantage of eliminating many types of electric noise and the effects of stray light. Another method is to employ a reference channel that passes some of the light through a non emitting fiber, such that all measurements are referenced to this channel. This has the advantage of greatly diminishing the effects of variations in the light source and electronic circuits, and effects in the fiber optics not originating in the emission strip. Various forms of display, recording and control can be provided.

BRIEF DESCRIPTION OF THE DRAWINGS

The invention will be readily understood by the following description of certain embodiments, by way of example, in conjunction with the accompanying drawings, in which.

DESCRIPTION OF THE PREFERRED EMBODIMENTS

Figure 1:
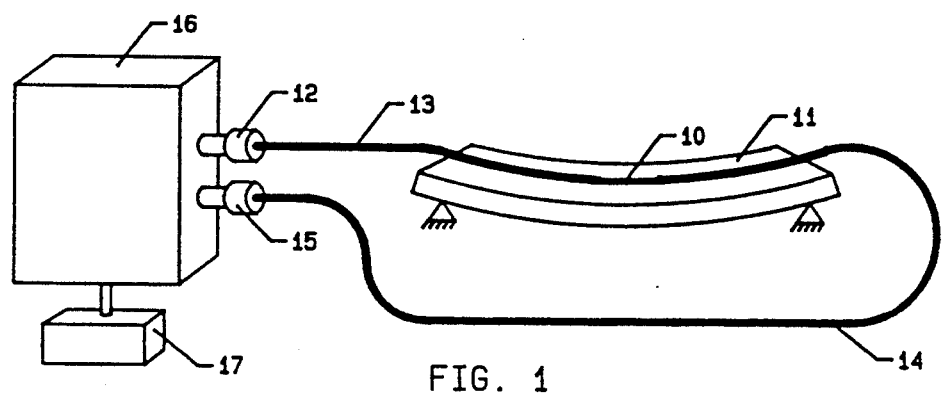
FIG. 1 is a diagrammatic illustration of a bending sensor apparatus, with the sensor shown cemented to a bending beam.

FIG. 1 illustrates a bending sensor 10 mounted with adhesive on bent beam 11. In the example, light is conveyed from a photo-emitter 12 through a plastic or other optical fiber light guide 13 to the sensor portion 10, and thence through guide 14 to a photo-detector 15. The light guide near the sensor region 10 has had its outer protective jacket removed, and the light conducting core exposed along a strip on the surface; portions 13 and 14 leading to the sensor region may have the jacket in place. The sensing portion 10 is adapted to sense bending. The photo-emitter 12 and photo-detector 15 are part of an electronic measuring system 16 and display 17, which includes means for measuring the difference in intensity of the light beam between the photo-emitter 12 and the photo-detector 15".

Figure 2:
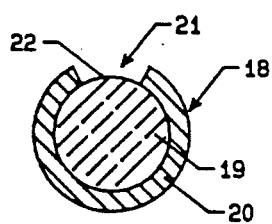
FIG. 2 is a cross-section through an optical fiber in accordance with the present invention.

FIG. 2 illustrates, in cross-section a conventional optical fiber wave guide 18 having a light conducting fiber 19 and a cladding 20. Normally there will be a buffer layer and a coating layer also. The cladding is removed locally, at 21, extending in a band along the fiber 19, to form a light emitting surface 22. The band can be formed by deliberately removing cladding as by abrasion, melting, etc. or by displacement as by pressure or rubbing on the fiber, for example by a heated tool, depending upon the particular form of fiber.

Figure 3:
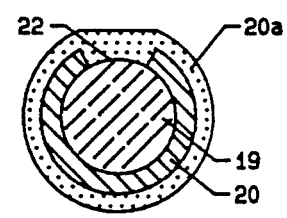
FIG. 3 is a cross-section similar to that of FIG. 2, illustrating a modification thereof.

FIG. 3 illustrates a modification of the arrangement of FIG. 2, in which the light emitting surface band 21 is covered with a light absorbant material 20a. Typical materials for the coating 20a are graphite filled epoxy resin, dye-filled resins and similar materials. The use of the coating 20a prevents emitted light interfering with any other instrument or structure and also prevents any back reflection into the fiber, which would affect the measurements. The additional coating 20a can be applied only over the band 21, but more commonly is applied around the entire fiber.

Figure 4:
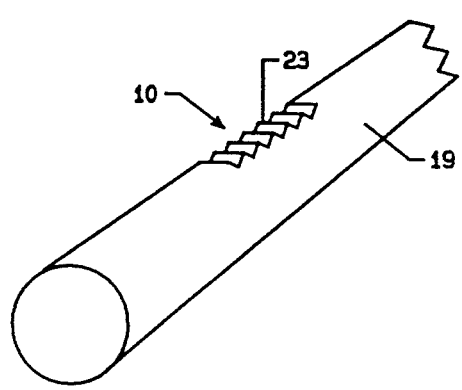
FIG. 4 is a perspective view, on a large scale, of part of a light guide showing a form of surface treatment.
Figure 5:
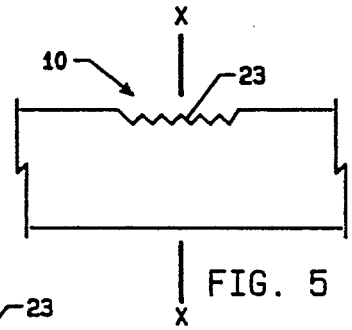
FIG. 5 is a side elevation of the light guide of FIG. 4.
Figure 6:
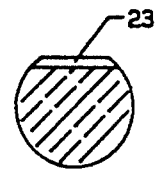
FIG. 6 is a transverse cross-section of the sensor as on line X—X in FIG. 5.

FIGS. 4, 5, and 6 illustrate one example of a fiber 19 with the emitting surface textured. Serrations 23 have been created on one side of the fiber, as by pressing it onto the surface of a file. Similar serrations can be created by heat forming and molding. Both plastic and glass optical fibers can be so formed. Heat forming can be accomplished by pressing the fiber slightly onto a heated metal surface which can be serrated, corrugated, or otherwise formed. The angle of the serrations can vary. It is not necessary to first remove the cladding of the fiber as this will be displaced. After treatment, a sensor portion emits some light along the length while transmitting a portion of any light within it to either end.

Figure 7:
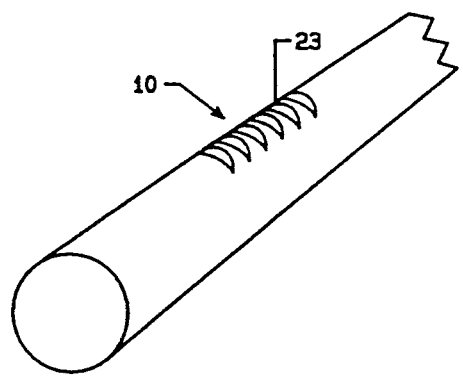
FIG. 7 illustrates an alternate form of surface treatment of the light guide.
Figure 8:
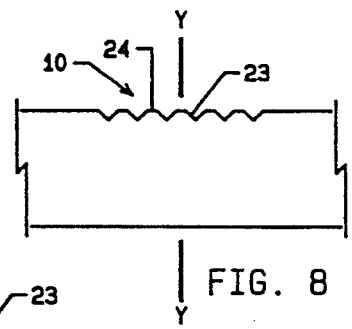
FIG. 8 is a side elevation of the light guide of FIG. 7.
Figure 9:
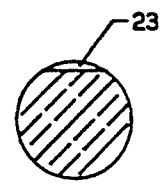
FIG. 9 is a transverse cross-section of the sensor as on line Y—Y of FIG. 8.

FIGS. 7, 8, and 9 illustrate another form of serration of a fiber 19. In this example the wedge-shaped serrations 23 of the sensing portion 10 are separated by small spaces 24. The exact shape of the serrations can vary considerably. Diamond-shaped serrations have also been successfully used. These are formed by pressing the fiber against a file with a pattern of intersecting serrations.

Alternatively, one side of the fiber can be abraded by sanding, sand-blasting, etching, or other means of removing or changing the cladding layer.

Figure 10:
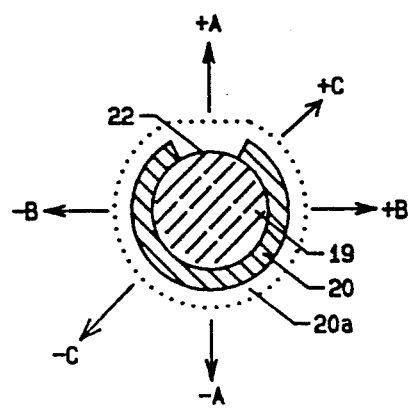
FIG. 10 is a transverse cross-section of a sensor showing the axes of maximum and minimum sensitivity to bends.

FIG. 10 illustrates the axes of maximum and minimum sensitivity, and the direction of signal change of a bending sensor. In this cross-section, the light emitting surface band is 22 at the top of the sensing section of the fiber. Bends within the vertical plane containing A—A produce the maximum change in transmission of light through the fiber. Thus A—A is called the axis of maximum sensitivity. For bends concave upward, the transmission increases. For bends concave downward, the transmission decreases. The minimum change in transmission occurs for bends in the horizontal plane containing B—B. Bends in this plane produce negligible change in transmitted light, so B—B is called the axis of minimum sensitivity. Intermediate response occurs for bends off the major axes, such as at C—C. This intermediate response is a cosine function of the angle between the plane of maximum sensitivity and the plane of the angle of the bend. In the figure, + and − signs have been placed to indicate increases and decreases in transmitted light relative to the transmission of the fiber when it is straight. The surface band 22 can be just bare fiber, as in FIG. 2, or textured, as, for example, in FIGS. 4 to 9.

Figure 11:
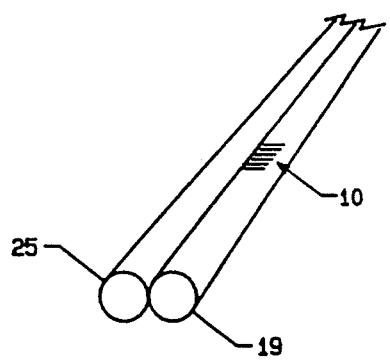
FIG. 11 is a perspective view of a sensor employing a non emitting reference fiber paired with an emitting, sensing, fiber.

FIG. 11 illustrates a sensor including a paired reference fiber. Fiber 19 has a sensing portion 10. Fiber 25 has no sensing portion. The pair are used in dual detection methods, where all measurements are referenced to the transmission through fiber 25. Because fiber 25 is arranged mechanically in the same way as fiber 19, most errors are eliminated from the measurement, by virtue of the fact that untreated fibers show little change in transmission for small bend angles (roughly less than 20°, whereas formed fibers are optimized for response to bending).

Figure 12:
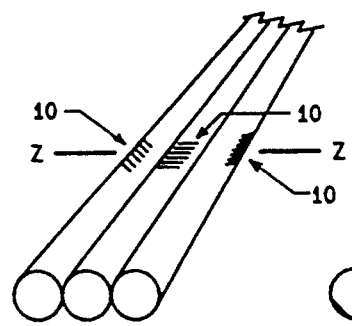
FIG. 12 is a perspective view of a triple sensor for detecting the three-dimensional bend vector.
Figure 13:
FIG. 13 is a cross-sectional view of the triple sensor on the line Z—Z of FIG. 12, showing the 120° arrangement of emitting sections.

FIG. 12 illustrates three fibers, arranged to form a sensing system capable of detecting the three-dimensional vector describing the applied bend. Each fiber has a light emission portion 10, just bare fiber or formed with serrations or abrasions. The sensing portions are arranged so that the axes of maximum sensitivity are at 120° to each other. FIG. 13 shows this relationship more clearly. Solving simultaneous equations for the magnitude and sign of the transmissions of the fibers will yield the three components of the bend vector of an element, such as a beam, to which the sensor has been affixed. Alternate arrangements of the fibers are possible, such as having the sensing portions facing at different angles, triangular rather than flat bundles, or having the fibers separated from one another. In the examples illustrated in FIGS. 11, 12 and 13, the fibers are conventional in that they are composed of the main fiber, of glass, plastic or other, with a cladding layer. The cladding layer is locally removed at the sensor positions 10 as mentioned above, by various means.

Figure 14:
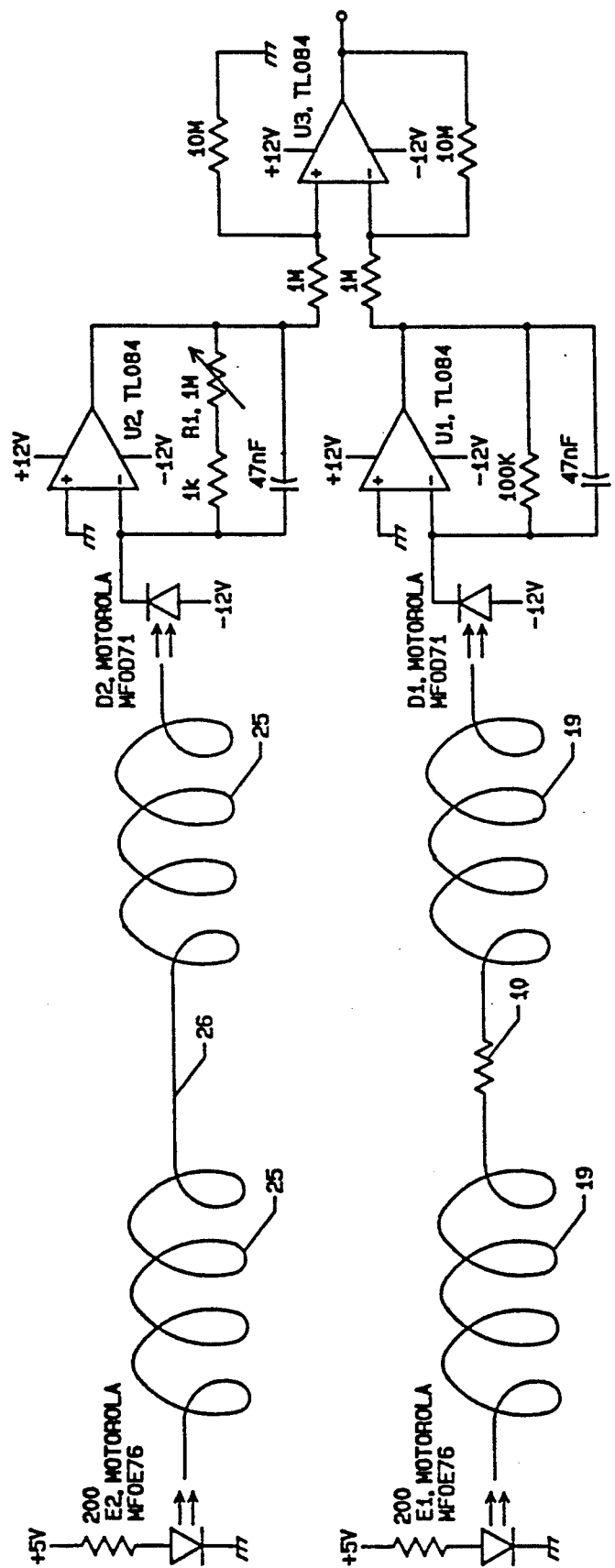
FIG. 14 is a schematic diagram showing light paths and electronic circuitry.

FIG. 14 illustrates one simple example of electronic circuitry that can be used to measure the transmission of light through a paired sensor element such as that shown in FIG. 11. In FIG. 14, fiber 19 (shown coiled to indicate arbitrary placement and length of the guide conveying light to and from the sensing portion) has the light emitting strip at 10. Fiber 25, which is otherwise the same as fiber 19, has no sensing portion at position 26, which represents a section of the fiber in close proximity to sensor section 10. Both fibers are illuminated by photoemitters E1 and E2, which are light emitting diodes. Photodetectors D1 and D2, which receive light from the fibers, are PIN photodiodes, back-biased with 12 Volts to enhance the speed of their response to light energy. U1 and U2 are high input impedance operational amplifiers arranged as transimpedance amplifiers, converting light energy linearly into voltages fed to the inputs of U3, which is an operational amplifier connected as a differential amplifier with a gain of 10. The gain of amplifier U2 can be varied with R1 so that for a straight fiber, the inputs to U3 are equal. In this condition, the optoelectronic circuit is analogous to a two-armed bridge such as is used to make strain-gauge measurements. Errors due to degradations in the fibers, connector variations, temperature fluctuations, and the like tend to cancel before reaching the output of U3. The output of U3 is a voltage which varies with bending at the band portion 10. The output voltage can be further amplified and sent to a display unit or used to control various parameters, such as actuators designed to minimize the angle of bend.

Many variations of the circuitry are possible, including variations with much greater immunity to error sources. One such variation would use the same light source and detector, separating the signals by chopping them at different frequencies and employing synchronous detection. Another variation is to replace U3 in FIG. 14 with a divider circuit, so that the sensor signal is divided arithmetically by the reference signal.

Figure 15:
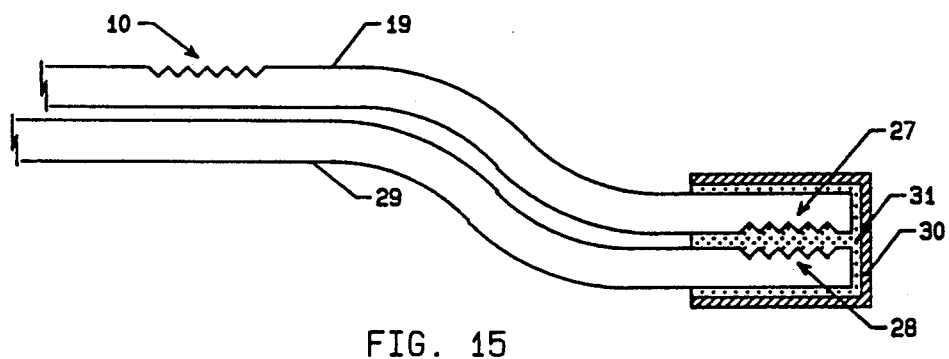
FIG. 15 shows an alternative form of the light guide return path.

FIG. 15 illustrates a variation of the sensor design which eliminates loops of light guide past the sensing portion. Light from a photo-emitter enters the system through guide 19 and passes through the sensing portion 10. Another sensing portion 27 faces sensing portion 28 on guide 29. An opaque cap 30 filled with optically clear adhesive 31, covers this junction area. Guide 29 carries light back to a photo-detector. The junction region at 27 and 28 is held rigidly by the cap and adhesive so that is does not respond to bending. This arrangement allows the use of parallel fibers without return loops, which can be an advantage when embedding the sensors in long, narrow structures.

Alternatively, a mirror can be used to reflect light from the distal end of the sensor fiber back into a return fiber. In another alternative, a directional coupler can be used with a single sensor fiber which has a mirror mounted at its distal end. The coupler is used to pass light to the proximal end of the fiber from the emitter, and to direct reflected light emanating from the proximal end of the fiber, into the detector. Typically, the directional coupler would be placed between the emitter, the detector, and the proximal end of the fiber.

Figure 16:
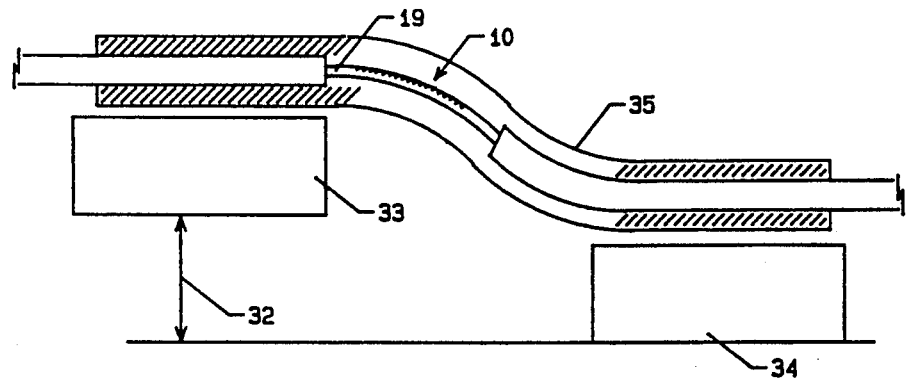
FIG. 16 shows an alternate application of the sensor, to measurement of position.

FIG. 16 illustrates the application of the bending sensor to the measurement of displacement. Vertical displacement 32 between blocks 33 and 34 (representing, for example, moving parts of a mechanical system), is measured by a bend-sensing region 10 in guide 19, cemented into flexible beam 35, which is attached to the two blocks. Similar fixturing, with or without a flexible beam, would enable the measurement of angles, such as pedal position, over a large range.

The advantages of the sensing devices described above are illustrated in FIGS. 17, 18, and 19. For these figures the sensors were fabricated from methyl methacrylate optical fiber, 1 mm in diameter. The black plastic jacket was left on the fiber except for a 50 mm section near the sensing portion, where the black plastic was removed.

Figure 17:
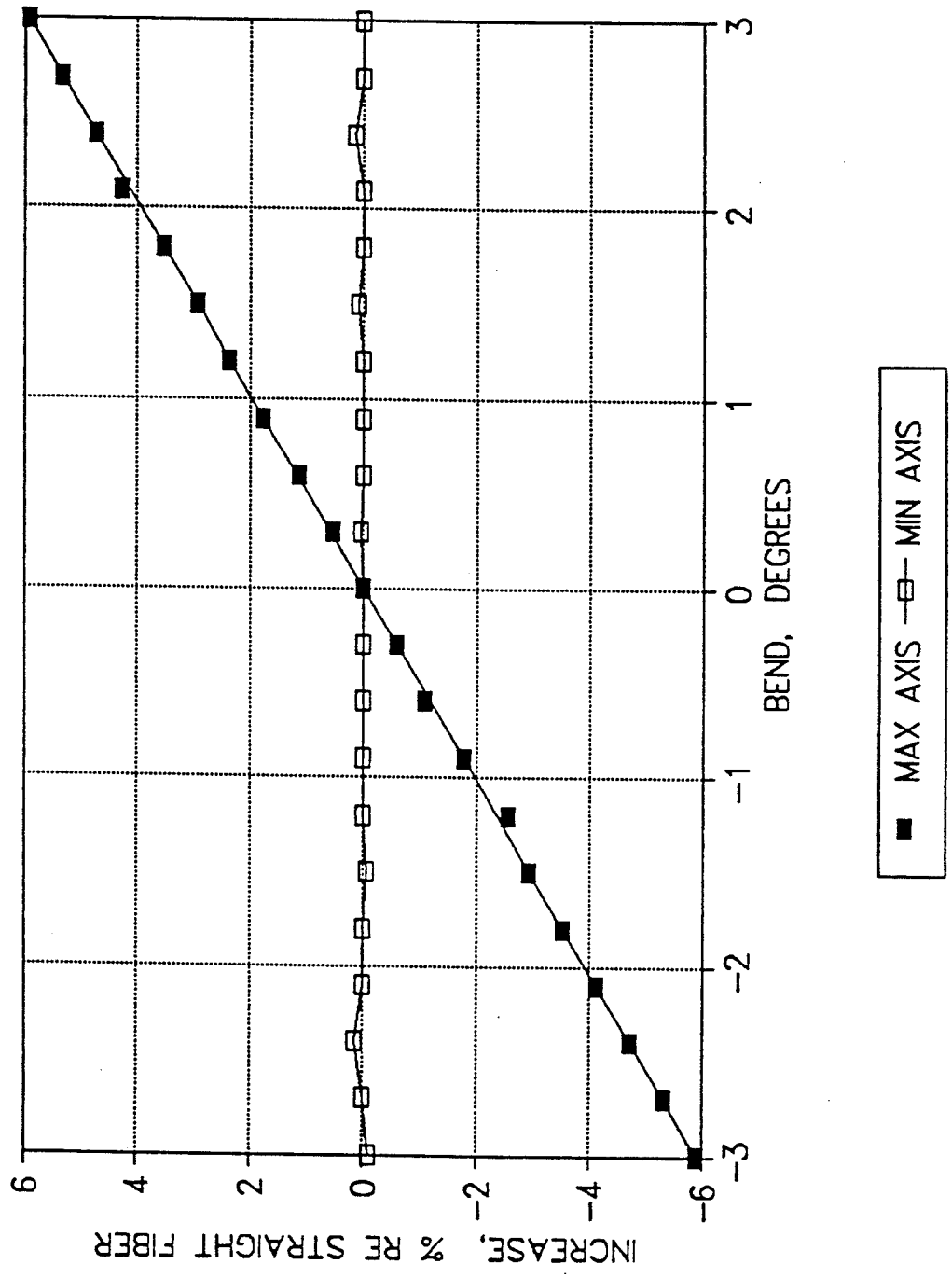
FIGS. 17, 18, and 19 are graphs of the percentage changes in transmission of light guides treated in various ways to sense bending.

FIG. 17 illustrates, by way of example, the percentage change in transmission, that is the amount of light transmitted compared to 100 percent for a straight fiber, of a 1 mm diameter plastic fiber formed over a 25 mm length with serrations and affixed with epoxy adhesive to a plastic beam. Weights were placed on the beam, which was clamped at one end, to produce the angular deflections shown on the horizontal axis of the graph. Two outputs of the sensor are shown. One is from the sensor when the beam is mounted to bend along the axis of maximum sensitivity (serrations pointing up); the other is the output when the beam is mounted to bend along the axis of minimum sensitivity (serrations pointing horizontally). There is virtually no sensitivity to bending along the axis of minimum sensitivity. The sensor response in the axis of maximum sensitivity is essentially linear with respect to angular deflection, increasing for upward bends and decreasing for downward bends.

The graph illustrates the sensitivity obtainable with very simple electronics (for example, as shown in FIG. 13). One could measure beam deflection with a strain gauge on the top of the beam. The strain gauge would be responding to elongation of the top surface of the beam rather than curvature of the top surface. The beam is undergoing an elongation of approximately 120 microstrain (microns per meter) along its top for a 3° deflection, indicating that the optical sensor is achieving a resolution of better than 12 microstrain (120 microstrain over 10 data points) for this experiment. Other sensors have been constructed which are capable of resolving less than 1 microstrain, which is the approximate lower sensitivity limit for strain gauges. Because it is possible to measure curvature with a bending sensor on the neutral axis of the beam, where there is, by definition, no strain, the lower limit for strain sensitivity is zero.

Figure 18:
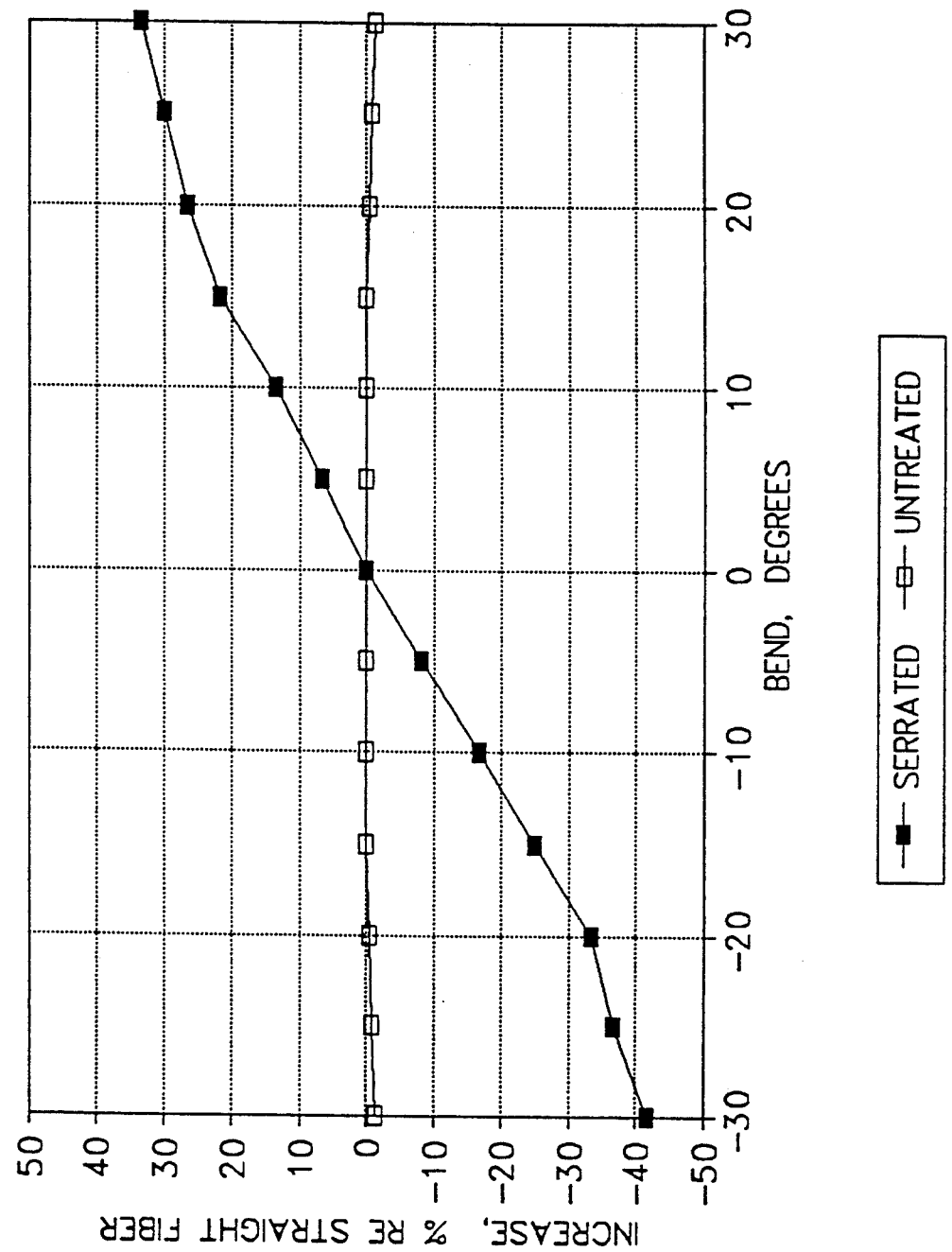

FIG. 18 illustrates, by way of example, the response of a fiber light guide having serrations over a 25 mm length compared to the response of an unformed fiber. The fibers were clamped near one end of the sensitive region and moved so as to bend in a loose curve of the total angle shown on the horizontal axis of the graph. The fiber with the sensing portion was moved in the plane of maximum sensitivity. The fiber demonstrates a large range of linear response; approximately ±20°. When moved similarly, the unformed fiber, an example of a microbend sensor, showed virtually no change with angle, except for angles over 20 degrees, where the response is approximately 20 times less than the formed fiber.

Figure 19:
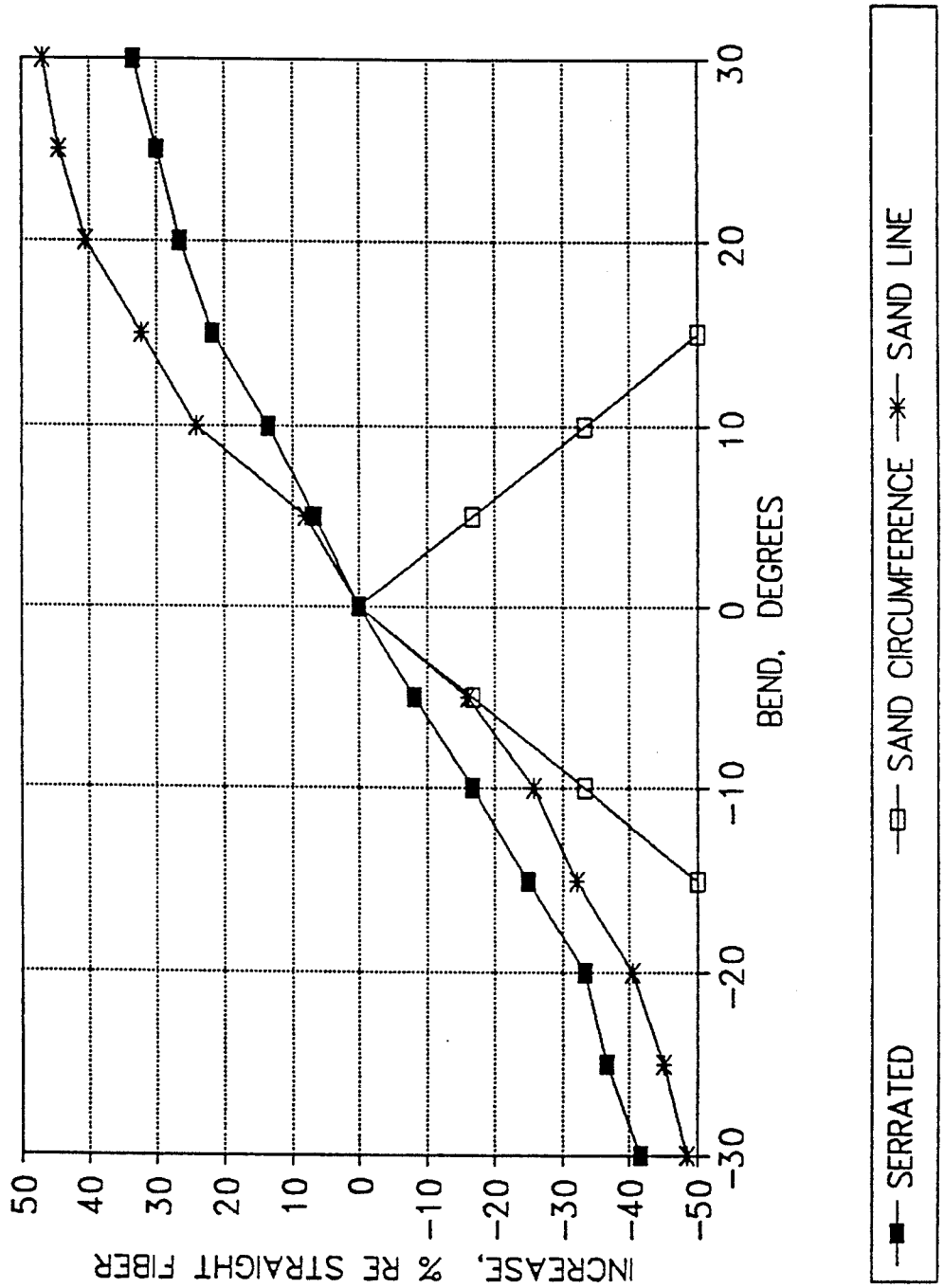

FIG. 19 illustrates, by way of example, the response of three fibers having the textured surface formed in different ways. The test setup is the same as for FIG. 17. The first fiber has serrations over a 25 mm length. The second is formed by abrading slightly with fine sandpaper around the circumference of the fiber over a 25 mm length. The third is formed by abrading slightly with the same sandpaper over a 25 mm length, but only on one side of the fiber, similar in overall shape to the region of serrations of the first fiber. The two fibers having the textured surface on one side show good preservation of direction of the bend in their responses The fiber having the textured surface on its entire surface shows no preservation of the direction of bend. It would have to be bent when mounted on a structure. The serrated fiber shows linearity of response over a wider range than the fiber sanded on one side.

Figure 20:
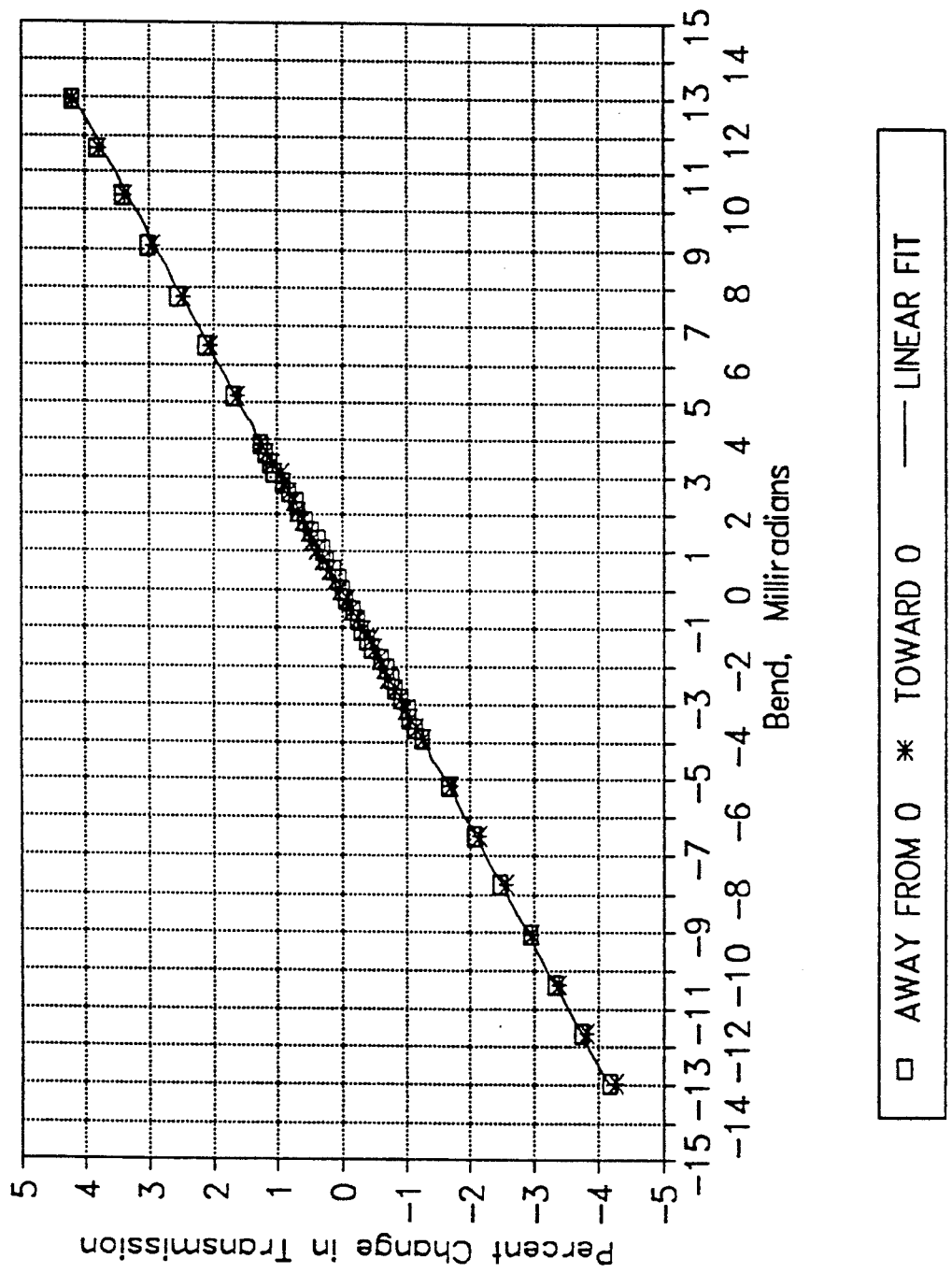
FIGS. 20 and 21 are graphs of the percentage changes in transmission for an opposed sensor pair made from two light guides.

FIG. 20 illustrates, by way of example, the response of a sensor pair mounted with epoxy adhesive inside a small piece of plastic tubing. Each sensor was formed by removing cladding along a strip on the side of a silica fiber core, 200 microns in diameter. The strip was 10 mm long. The two strips were coated with graphite-filled epoxy and arranged to face in opposite directions, so that response to bends was of opposite polarity but approximately equal magnitude for each sensor. The "percentage change in transmission" shown in FIG. 20 refers to the difference in the two electrical signals resulting from light transmission changes in the two sensors, as a percentage of the electrical signal from one sensor at rest. This paired method of measurement is one means of greatly decreasing the effects of common-mode emitter and detector drift. In this example, the tubing was first bent, by means of a micrometer drive, upward in the plane of maximum sensitivity (positive horizontal graph axis), away from its rest position (zero on horizontal axis). Next it was moved back toward its rest position. These steps were repeated for downward bends. The data points in FIG. 20 illustrate the excellent linearity of the system, and the low hysteresis ("away from zero" and "toward zero" points are nearly coincident). A straight line ("Linear Fit") has been drawn on FIG. 20 to illustrate the excellent linearity of response.

Figure 21:
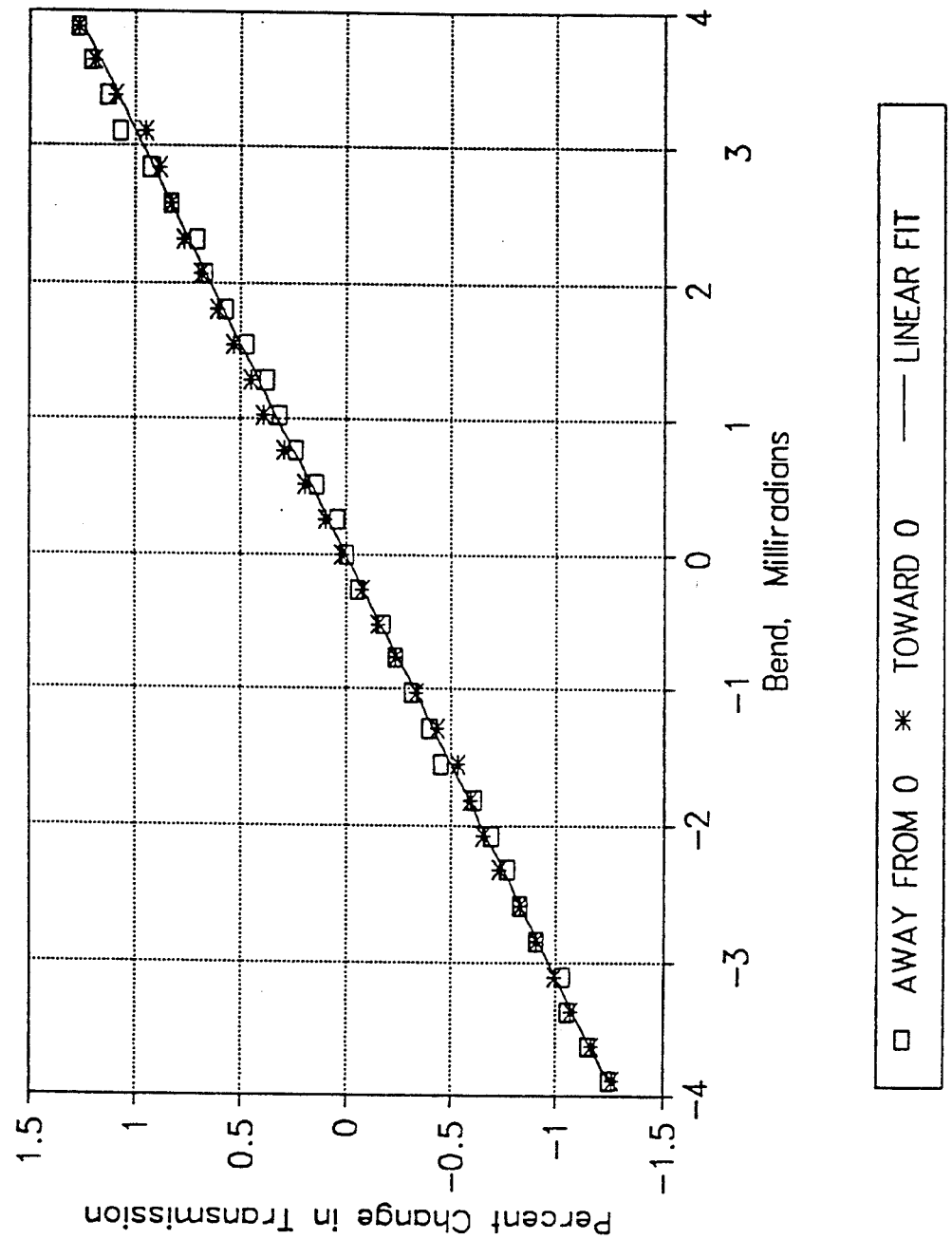

FIG. 21 shows the same data points as FIG. 20, over a small range of bends near the origin.

The response of sensors is explained in the following way: Light rays travel along fiber optics throughout a range of angles limited by the difference in index of refraction between the core and the cladding. For straight fibers, some light rays pass through the emission band. As a fiber with the emission band at the top bends downward, more of the rays impinge on the band at angles capable of passing through the surface, either by diffusion or by direct transmission. As the fiber bends upward, fewer rays will impinge on the band, and will be at shallow angles to its surface, so that more of them stay within the fiber, refracting from the untreated core/cladding boundary toward the fiber outside the sensor region. Bends at right angles to the axis of maximum sensitivity change to a minimum degree the amount of light striking the emission band, so there is virtually no change in transmitted light.

The width of the emission band around the circumference of the fiber will determine the sensitivity of the fiber to bends, with wider bands producing a larger percentage change per degree of bend. However, very wide bands will tend to increase the sensitivity to bends in the axis of minimum sensitivity. Typical sensors have emission bands that cover 5° to 30° of the circumference of the fiber, but other values will work. The length of the emission band can vary. It can be any length from millimeters to meters but there is less gain in sensitivity for long lengths, than expected. There is an optimum length for the strip, which is a function of the diameter of the fiber, its emission band width, and the minimum linear deflection angle desired. For 1 mm fibers, the optimum is about 25–50 mm, and for 200 micron fibers, it is about 10–20 mm. Long sensors can be formed by alternating lengths of fibers with an emission strip with lengths of fully clad fibers. Short sensors will be less sensitive, but more specific as to location of bend along the length of the member to which they are attached. However very short sensors can be made, such as 8 mm sensors on 125 micron fibers.

Sensors in accordance with the invention have various advantages, and useful characteristics. No special electronics are required to measure interference patterns, it is only necessary to measure the amount of light transmitted. Cost is orders of magnitude below that for interference (OTDR) techniques. Sensitivity is in the same range as that of resistance strain gauges. For many situations, particularly when the sensors are mounted near the neutral axis of a bending beam, changes in signal per microstrain are greater than those for resistance strain gauges, as measured in percent. The linear range is very large. They are particularly suited to measurement of bending in aircraft wings, helicopter blades, machinery, robot arms, or large structures. They are not affected by temperature, since measurement is not dependent on small changes in length of the fiber or its sensing portion. This is a distinct advantage over resistance strain gauges, which have a relatively narrow range of temperature resistivity unless compensated, and over interference techniques, which are affected even more by temperatures than are resistance gauges. They can be used to measure position, with a large dynamic range.

What is claimed is:

1. A fiber optic bending, and positioning, sensor comprising a fiber optic guide having a light emission surface extending in a thin band on a side of the fiber for at least part of its length, said light emission surface covered by a coating of light absorbent material.

2. A sensor as claimed in claim 1, said light emission surface comprising a textured surface.

3. A sensor as claimed in claim 2, said textured surface comprising a serrated surface, the serrations extending transversely of the axis of the light guide.

4. A sensor as claimed in claim 1, including means for injecting a light beam into one end of said light guide and means for detecting said light beam at the other end of said light guide.

5. A sensor as claimed in claim 4, including means for measuring the difference in intensity of said light beam between said one end and said other end of said light guide.

6. A sensor as claimed in claim 5, including display means for indicating any said difference in intensity of said light beam as a bending or displacement of said light guide.

7. A sensor a claimed in claim 1, including a further fiber optic light guide positioned alongside said fiber optic light guide, said further light guide having an unbroken cladding layer and forming a reference light guide.

8. A sensor as claimed in claim 1, comprising a plurality of said fiber optic light guides, each having a light emission surface extending in a thin band on a side of the fiber, said thin bands oriented in different directions, at predetermined angles relative to each other.

9. A sensor as claimed in claim 1, comprising three fiber optic guides, extending alongside each other in a parallel array, each light guide having a light emission surface extending in a thin band on a side of the fiber for at least part of its length, said thin bands oriented at approximately 120° to each other.

10. A sensor as claimed in claim 5, said measuring means adapted to indicate bending of a member to which the sensor is attached.

11. A sensor as claimed in claim 5, said measuring means adapted to indicate displacement of one end of a member, to which the sensor is attached, relative to its other end.

12. A method of sensing bending, and displacement, of an elongate member, comprising attaching a fiber optic light guide to said member, said light guide having a light emission surface extending in a thin band on a side of the fiber at least part of its length, said light guide extending along said member; injecting a light beam into one end of said light guide, detecting said light beam at the other end of said light guides, and measuring the difference in intensity of said light beam between said one end and said other end, indicating bending, or displacement, of said member.

13. The method of claim 12, including attaching a plurality of fiber optic light guides to said elongate member, each having a light emission surface extending in a thin band, said bands oriented at predetermined angles to each other.

14. The method as claimed in claim 13, including three fiber optic light guides, said bands oriented at about 120° to each other.

15. The method as claimed in claim 12, including attaching a further fiber optic light guide alongside said fiber optic light guide, said further fiber optic light guide acting as a reference light guide.

16. Apparatus for sensing, and indicating, bending or displacement of a member, comprising: a fiber optic wave guide having a light emission surface extending in a thin band on a side of the fiber, means for mounting said wave guide on said member, means for injecting a light beam into one end of said wave guide; means for detecting transmitted light at the other end of said wave guide; and means for measuring the difference in intensity of said light beam between said one end and said other end of said wave guide.

17. A sensor as claimed in claim 16, said light emission surface comprising a textured surface.

18. A sensor as claimed in claim 17, said textured surface comprising a serrated surface, the serrations extending transversely of the axis of the light guide.

19. A sensor as claimed in claim 16, including display means for indicating any said difference in intensity of said light beam as a bending or displacement of said light guide.

20. A sensor as claimed in claim 16, including a further fiber optic guide positioned alongside said fiber light guide, said further light guide having an unbroken cladding layer and forming a reference light guide.

21. A sensor as claimed in claim 16, comprising a plurality of said fiber optic light guides, each having a light emission surface extending in a thin band on a side of the fiber, said thin bands oriented in different directions, at predetermined angles relative to each other, means for injecting a light beam into one end of each light guide, means for detecting transmitted light at the other end of each light guide, and means for measuring the difference in intensity of said light beams between said one end and said other end of each light guide.

22. A sensor as claimed in claim 21, comprising three fiber optic light guides, extending alongside each other in a parallel array, each wave light having a light emission surface extending in a thin band on a side of the fiber for at least part of its length, said thin bands oriented at approximately 120° to each other.

23. A sensor as claimed in claim 16, said measuring means adapted to indicate bending of a member to which the sensor is attached.

24. A sensor as claimed in claim 16, said measuring means adapted to indicate displacement of one end of a member, to which the sensor is attached, relative to its other end.

25. A sensor as claimed in claim 16, including a layer of light absorbent material on said light emission surface.

* * * * *